United States Patent [19]

Fodor et al.

[11] Patent Number: 5,591,863
[45] Date of Patent: Jan. 7, 1997

[54] IMIDAZOLIUM HARDENERS FOR HYDROPHILIC COLLOIDS

[75] Inventors: Ludovic Fodor; Timothy D. Weatherill, both of Hendersonville; Rolf T. Weberg, Brevard, all of N.C.

[73] Assignee: Sterling Diagnostic Imaging, Inc., Glasgow, Del.

[21] Appl. No.: 463,793

[22] Filed: Jun. 5, 1995

Related U.S. Application Data

[63] Continuation of Ser. No. 266,403, Jun. 27, 1994, Pat. No. 5,470,986.

[51] Int. Cl.$^6$ ............... C07D 233/64; C07D 233/61; C07D 233/72; B05D 3/02
[52] U.S. Cl. ............... 548/312.7; 427/397; 430/446; 430/451; 430/510; 430/539; 430/626; 430/642; 548/313.7; 548/334.1
[58] Field of Search ............... 548/312.7, 313.7, 548/334.1; 427/397; 430/539, 642, 626, 510, 451, 446

[56] References Cited

U.S. PATENT DOCUMENTS

| | | | |
|---|---|---|---|
| 3,288,775 | 11/1966 | Anderau et al. | 260/117 |
| 3,325,287 | 6/1967 | Yamamoto et al. | 96/111 |
| 3,444,138 | 5/1969 | Williams | 260/65 |
| 3,549,377 | 12/1970 | Meckl et al. | 96/111 |
| 3,853,907 | 12/1974 | Edwards | 260/309 |
| 3,855,235 | 12/1974 | McConnell | 260/309.6 |
| 3,887,476 | 6/1975 | McConnell | 252/8.75 |
| 4,041,019 | 8/1977 | McGraw et al. | 260/75 |
| 4,181,529 | 1/1980 | Sels et al. | 430/626 |
| 4,187,114 | 2/1980 | Kokelenberg et al. | 430/510 |
| 4,216,108 | 8/1980 | Sels et al. | 252/182 |
| 4,404,379 | 9/1983 | Hajek et al. | 544/231 |
| 4,684,736 | 8/1987 | Töpfl | 548/309 |
| 4,710,456 | 12/1987 | Naoi et al. | 430/564 |
| 4,758,671 | 7/1988 | Dvorsky et al. | 548/341 |
| 4,874,687 | 10/1989 | Itabashi | 430/446 |
| 4,944,966 | 7/1990 | Jerenz | 427/397 |
| 5,145,983 | 9/1992 | West | 548/341 |
| 5,378,842 | 1/1995 | Fodor et al. | 544/139 |

FOREIGN PATENT DOCUMENTS

| | | | |
|---|---|---|---|
| 0519329 | 12/1992 | European Pat. Off. | 544/139 |
| 0576911 | 1/1994 | European Pat. Off. | 544/139 |
| 0576912 | 1/1994 | European Pat. Off. | 544/139 |
| 3-277632 | 12/1991 | Japan | C08G 73/06 |
| 1408344 | 10/1975 | United Kingdom | C07D 233/56 |
| 92/22535 | 12/1992 | WIPO | C07D 233/16 |

Primary Examiner—Floyd D. Higel
Attorney, Agent, or Firm—Joseph T. Guy, Jr.

[57] ABSTRACT

This invention is related to improved hardeners for proteinaceous materials. More specifically this invention is related to improved imidazolium hardeners for crosslinking a proteinaceous material for use in a photographic film. The improved hardeners are defined by the formula:

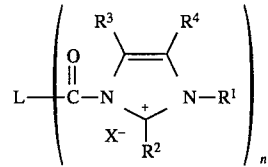

17 Claims, No Drawings

IMIDAZOLIUM HARDENERS FOR HYDROPHILIC COLLOIDS

CROSS REFERENCES TO RELATED APPLICATIONS

This is a continuing application of U.S. patent application Ser. No. 08/266,403 filed Jun. 27, 1994 now U.S. Pat. No. 5,470,986.

BACKGROUND OF THE INVENTION

1. Field of the Invention

This invention is related to improved hardeners for proteinaceous materials. More specifically this invention is related to improved imidazolium hardeners for crosslinking a proteinaceous material for use in a photographic film.

2. Description of the Related Art

Proteinaceous materials are used for a wide variety of applications. One of the predominant useful properties is their ability to dissolve in aqueous solutions and yet form a solid matrix which is permeable to aqueous solutions upon drying. These properties have been exploited for many generations in the field of photographic sciences and proteinaceous materials are still widely used as a binder for harboring silver halide grains in the photosensitive layer of most photographic films.

Formation of a solid matrix is typically considered to be a result of inter-and intra-molecular hydrogen bonding within both the crystalline and amorphous regions of proteinaceous materials. If only the natural hydrogen bonding is employed, the strength of the wetted matrix is typically insufficient for use in a photographic film. Therefore, it is common practice to add a crosslinking agent, also known as a hardener, to a protein material when used for photographic layers.

Hardeners are chosen, in part, for their ability to link one group on a protein molecule with another group on the same, or different, protein molecule. The linking generates a three-dimensional network of proteinaceous material. This three-dimensional network has sufficient integrity to allow swell during processing without causing detrimental effects to the silver halide grain harbored therein. Another important aspect of the three-dimensional network is an ability to allow solution to permeate freely during the photographic processing steps of development, fix (or bleach) and wash. It is also imperative that the aqueous solution which freely permeates the matrix is not strongly absorbed. A matrix with high affinity to water, or other solutions is more difficult to dry. This is particularly important for photosensitive elements since they must often be capable of transiting the photographic processing steps of development, fix, wash and dry in 20–120 sec. Carboxyl groups can be the dominant hydrophilic species on a proteinaceous molecule. Carboxyl groups are either pendant to the proteinaceous molecule, or integral to a side chain. It is therefore desirable to alter the carboxyl groups in some way to decrease the water affinity of the matrix.

Peptide couplers are known in the art to couple two regions of hydrophilic colloid thereby creating the aforementioned three-dimensional network as a compilation of interconnected strands of hydrophilic colloid. A particular advantage of peptide couplers is their ability to couple a carboxyl group with an amine group to form an amide bond between two portions of the proteinaceous material. This has many benefits including increasing the strength of the cross-linked matrix and decreasing the number of unreacted carboxyl groups and thus the overall water affinity of the matrix.

In addition to crosslinking the proteinaceous material, it is often desirable to further augment this hydrophilic colloid network with other ingredients such as hydrophilic or hydrophobic groups, dyes, plasticizers and the like. Previously, the augmentation has taken one of several forms. Either an adjuvant is admixed with the hydrophilic colloid or the gelatin is derivatized to include pendant groups which can impart specific properties to the gelatin. Admixed ingredients can typically leach out during any wet procedure and can also diffuse through the matrix structure to decrease their effectiveness. Many times the admixed ingredients are not permanent. Derivatizing is detailed in EP 576,912A and EP 576,911A. A derivatization reaction typically utilizes a crosslinking site and therefore decreases the number of carboxyl or amine groups available for crosslinking. A decrease in the number of available crosslinking sites could affect the amount of crosslinked matrix and subsequently decrease the strength of the binder.

There has been a long felt need in the art to provide a hardener which can effectively incorporate additives to the hydrophilic colloid layer while concurrently crosslinking the strands of hydrophilic colloid. There has been a particular need to incorporate additives as a bridge between two strands of hydrophilic colloid. These bridge groups can be dual purpose since they act as crosslinkers and may impart other properties to the hydrophilic colloid layer.

SUMMARY OF THE INVENTION

It is an object of the present invention to provide an improved hardener for a hydrophilic colloid.

It is another object of the present invention to provide an improved hardener which can react with a multiplicity of pendant groups on hydrophilic colloids to form a bridge between the hydrophilic colloids.

It is another object of the present invention to provide an improved hardener which can be prepared rapidly.

A particular feature of the rapid preparation is the ability to be formed in-situ without the necessity for a separate preparation and isolation.

It is yet another object of the present invention to provide an improved hardener which can form a bridge between hydrophilic colloids wherein the bridge may impart specific properties to the hardened hydrophilic colloid.

A particular feature of the bridge is the ability to act as a mordanted additive such as a dye, polyalkylene oxide, hydrophobic group or other photographically useful group.

These and other advantages will be apparent from the disclosure wherein provided is a hardener for hydrophilic colloid defined by the formula:

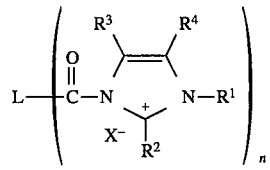

wherein:

L is chosen from a set consisting of alkyl of 1 to 20 carbons with a proviso that L is not —CH$_2$CHOH— or —CH$_2$CHCH$_2$—; phenyl; naphthyl; diphenyl;

anthracene; phenanthrene; benzyl; —$R^{11}$—O—$R^{12}$—; —$(R^{13}O)_m R^{14}$—; —$R^{15}SR^{16}$—;

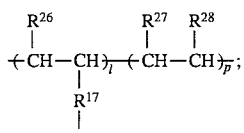

$N(R^{18})_{4-q}(R^{19})_q^+$;

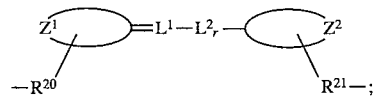

and

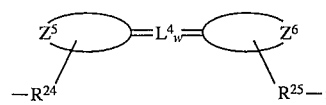

$R^1$ is an alkyl of 1 to 24 carbons; aryl of 6 to 24 carbons; aralkyl of 7 to 25 carbons; or —C(O)$R^5$;

$R^2$ is hydrogen; alkyl of 1 to 24 carbons; aryl of 6 to 24 carbons; aralkyl of 7 to 25 carbons; —O$R^6$; nitro; carboxyl; mercapto; alkylamino of 1 to 24 carbons; or a halogen;

$R^3$ and $R^4$ independently represent hydrogen; alkyl of 1 to 24 carbons; nitro; carboxyl; mercapto; —O$R^7$; or $R^3$ and $R^4$ taken together represent a 5- or 6-membered ring containing atoms chosen from a set consisting of C, N, O and S;

$R^5$ represents an alkyl of 1 to 24 carbons; aryl of 6 to 24 carbons; aralkyl of 7 to 25 carbons; —O$R^8$; —CN; —N$R^9 R^{10}$; or a 5- or 6-membered ring containing atoms chosen from a set consisting of C, N, O and S;

$R^6$ represents hydrogen or alkyl of 1 to 24 carbons;

$R^7$ represents hydrogen or alkyl of 1 to 24 carbons;

$R^8$ represents hydrogen; alkyl of 1 to 24 carbons or aryl of 6 to 24 carbons;

$R^9$ and $R^{10}$ independently represent hydrogen; alkyl of 1 to 24 carbons; aryl of 6 to 24 carbons; aralkyl of 7 to 25 carbons; or $R^9$ and $R^{10}$ taken together represent a 5- or 6-membered ring containing atoms chosen from a set consisting of C, N, O and S;

$R^{11}$ and $R^{12}$ independently represent alkyl of 2 to 24 carbons or aryl of 6 to 24 carbons;

$R^{13}$ and $R^{14}$ independently represent alkyl of 1 to 10 carbons;

$R^{15}$ and $R^{16}$ independently represent alkyl of 1 to 24 carbons;

$R^{17}$ represents a chemical bond; an alkyl of 1 to 24 carbons; an aryl of 6 to 24 carbons; or —$N(R^{29})_{3-s}(R^{30})_s^+$;

$R^{18}$ is an alkyl of 1 to 24 carbons;

$R^{19}$ is an alkylene of 1 to 24 carbons;

$R^{20}$, $R^{21}$, $R^{22}$, $R^{23}$, $R^{24}$ and $R^{25}$ independently represent a chemical linkage; an alkyl of 1 to 10 carbons; an aryl of 6 to 24 carbons; an aralkyl of 7–24 carbons; or an alkoxy of 1 to 10 carbons;

$R^{26}$, $R^{27}$ and $R^{28}$ independently represent hydrogen or alkyl of 1 to 5 carbons;

$R^{29}$ represents hydrogen or an alkyl of 1 to 20 carbons;

$R^{30}$ represents an alkylene of 1 to 20 carbons; arylene of 6 to 24 carbons; or aralkylene of 6 to 24 carbons;

$L^1$ represents methine or nitrogen;

$L^2$ and $L^3$ independently represent methine or dimethine;

$L^4$ represents dimethine;

$Z^1$, $Z^2$, $Z^3$, $Z^4$, $Z^5$ and $Z^6$ independently represent thiazoline; thiazalidine; benzothiazole; benzoxazole; 3-3-dialkylindolenine; 3,3-dialkylbenz[e]indole; 1,3-indandione; pyrazolone; 2,4,6,-trioxohexahydropyrimidine; 2-thio-4,6,dioxohezahydropyrimidine; 3,5-pyrazolidinedione; 5,7-dioxo-6,7-hyhydro-5-thiazolo[3,2-a]pyrimidine, 2-thio-2,4-oxazolidinedione; 5,5-dialkyl-1, 3-dyclohexanedione; 2-hydroxy-4H-pyrido[1,2-a]pyrimidin-4-one; rhodanine; hydantoin; thiohydantoin; or isoxazolone;

l is an integer of 2 to 400,000;

m is an integer of 1 to 40;

n is an integer of at least 2;

p is an integer of 0 to 400,000;

w is an integer of 0 to 5;

v is an integer of 0 to 5;

q is an integer of 2 to 4;

r is an integer of 0 to 5;

s is an integer of 1 to 3; and $X^-$ is a counter ion to balance charge.

A preferred embodiment is provided in a hardener for hydrophilic colloid defined by the formula:

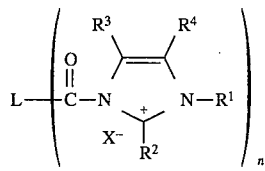

wherein:

L is chosen from a set consisting of alkyl of 1 to 20 carbons with a proviso that L is not —$CH_2CHOH$— or —$CH_2CHCH_2$—; phenyl; naphthyl; diphenyl; anthracene; phenanthrene; benzyl; —$R^{11}$—O—$R^{12}$—; —$(R^{13}O)_m R^{14}$—; —$R^{15}SR^{16}$—;

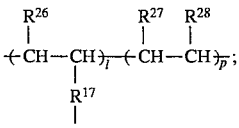

and $N(R^{18})_{4-q}(R^{19})_q^+$;

$R^1$ is an alkyl of 1 to 24 carbons; aryl of 6 to 24 carbons; aralkyl of 7 to 25 carbons; or —C(O)$R^5$;

$R^2$ is hydrogen; alkyl 1 to 24 carbons; aryl of 6 to 24 carbons; aralkyl of 7 to 25 carbons; —O$R^6$; nitro; carboxyl; mercapto; alkylamino of 1 to 24 carbons; or a halogen;

$R^3$ and $R^4$ independently represent hydrogen; alkyl of 1 to 24 carbons; nitro; carboxyl; mercapto; —O$R^7$; or $R^3$ and $R^4$ taken together represent a 5- or 6-membered ring containing atoms chosen from a set consisting of C, N, O and S;

$R^5$ represents an alkyl of 1 to 24 carbons; aryl of 6 to 24 carbons, aralkyl of 7 to 25 carbons; —$OR^8$; —CN; —$NR^9R^{10}$; or a 5- or 6-membered ring containing atoms chosen from a set consisting of C, N, O and S;

$R^6$ represents hydrogen or alkyl of 1 to 24 carbons;

$R^7$ represents hydrogen or alkyl of 1 to 24 carbons;

$R^8$ represents hydrogen; alkyl of 1 to 24 carbons; or aryl of 6 to 24 carbons;

$R^9$ and $R^{10}$ independently represent hydrogen; alkyl of 1 to 24 carbons; aryl of 6 to 24 carbons; aralkyl of 7 to 25 carbons; or $R^9$ and $R^{10}$ taken together represent a 5- or 6-membered ring containing atoms chosen from a set consisting of C, N, O and S;

$R^{11}$ and $R^{12}$ independently represent alkyl of 2 to 24 carbons or aryl of 6 to 24 carbons;

$R^{13}$ and $R^{14}$ independently represent alkyl of 1 to 10 carbons;

$R^{15}$ and $R^{16}$ independently represent alkyl 1 to 24 carbons;

$R^{17}$ represents a chemical bond; an alkyl of 1 to 24 carbons; an aryl of 6 to 24 carbons; or —$N(R^{29})_{3-s}(R^{30})_s^+$;

$R^{18}$ is an alkyl of 1 to 24 carbons;

$R^{19}$ is an alkylene of 1 to 24 carbons;

$R^{26}$, $R^{27}$ and $R^{28}$ independently represent hydrogen or alkyl of 1 to 5 carbons;

$R^{29}$ represents hydrogen or an alkyl of 1 to 20 carbons;

$R^{30}$ represents an alkylene of 1 to 20 carbons; arylene of 6 to 24 carbons; or aralkylene of 6 to 24 carbons;

l is an integer of 2 to 400,000;

m is an integer of 1 to 40;

n is an integer of at least 2;

p is an integer of 0 to 400,000;

q is an integer of 2 to 4;

s is an integer of 1 to 3; and $X^-$ is a counter ion to balance charge.

DETAILED DESCRIPTION OF THE INVENTION

Hardeners of the present invention are represented by:

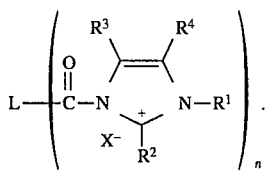

Compound I

L is an n-valent linking group connecting "n" carboimidazolium groups. Preferably L comprises an alkylene, or substituted alkylene, of 1 to 24 carbons; aryl, or substituted aryl, of 6 to 24 carbons; aralkyl or substituted aralkyl of 7 to 25 carbons; ether or substituted ether of 2 to 40 carbons; thioether or substituted thioether of 2 to 40 carbons; amines or substituted amines of 2 to 24 carbons; the atoms chosen from C, N, O and S necessary to form a substituted or unsubstituted 5- or 6-membered ring; polyalkylene oxide, or substituted polyalkylene oxide, of 2 to 48 carbons; polyethylene or substituted polyethylene; alkylammonium, or substituted alkylammonium, of 4 to 24 carbons.

More preferably L comprises substituted or unsubstituted alkyl of 1 to 20 carbons; substituted or unsubstituted phenyl; substituted or unsubstituted naphthyl; substituted or unsubstituted diphenyl; substituted or unsubstituted anthracene; substituted or unsubstituted phenanthrene; substituted or unsubstituted benzyl; substituted or unsubstituted —$R^{11}$—O—$R^{12}$—; substituted or unsubstituted —$(R^{13}O)_mR^{14}$—; substituted or unsubstituted —$R^{15}SR^{16}$—;

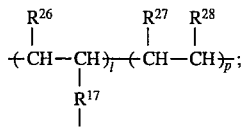

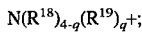

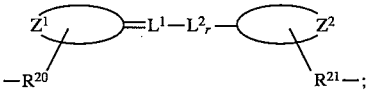

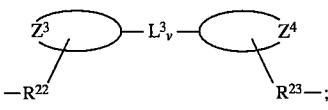

or

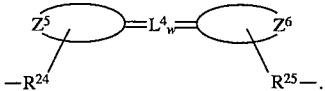

$R^1$ is an alkyl or substituted alkyl of 1 to 24 carbons; aryl or substituted aryl of 6 to 24 carbons; aralkyl or substituted aralkyl of 7 to 25 carbons; the atoms chosen from C, N, O, and S necessary to form a substituted or unsubstituted 5- or 6-membered ring; or —$C(O)R^5$. Preferably $R^1$ represents an alkyl or substituted alkyl or 1 to 10 carbons; the atoms chosen from C, N, O, and S necessary to form a substituted or unsubstituted 5- or 6-membered ring; or —$C(O)R^5$. Most preferably $R^1$ represents an alkyl or substituted alkyl of 1 to 5 carbons; the atoms chosen from C, N, O, and S necessary to form a substituted or unsubstituted 5- or 6-membered ring; or —$C(O)R^5$.

$R^2$ is hydrogen; alkyl, or substituted alkyl, of 1 to 24 carbons; aryl, or substituted aryl, of 6 to 24 carbons; aralkyl, or substituted aralkyl, of 7 to 25 carbons; —$OR^6$; nitro; carboxyl; mercapto; alkylamino, or substituted alkylamino, of 1 to 24 carbons; the atoms chosen from C, N, O and S necessary to from an unsubstituted or substituted 5- or 6-membered ring; or halogen. Preferably $R^2$ represents hydrogen; alkyl, or substituted alkyl, of 1–3 carbons; aryl, or substituted aryl, of 6–10 carbons; aralkyl, or substituted aralkyl, of 7–11 carbons. Most preferably $R^2$ represents hydrogen or alkyl of 1–3 carbons.

$R^3$ and $R^4$ may independently represent hydrogen; alkyl, or substituted, alkyl of 1 to 24 carbons; nitro; carboxyl; mercapto; —$OR^7$; $R^3$ and $R^4$ may independently represent the atoms chosen from C, N, O, and S necessary to form a substituted or unsubstituted 5- or 6-membered ring; or $R^3$ and $R^4$ may be taken together to represent the atoms chosen from C, N, O, and S necessary to form a substituted, or unsubstituted, 5- or 6-membered ring. Preferably $R^3$ and $R^4$ independently represent hydrogen, alkyl or substituted alkyl of 1–4 carbon atoms.

$R^5$ represents an alkyl or substituted alkyl of 1 to 24 carbons, aryl or substituted aryl of 6 to 24 carbons, aralkyl or substituted aralkyl of 7 to 25 carbons; —$OR^8$; —CN; —$NR^9R^{10}$; or the atoms chosen from C, N, O and S necessary to form a substituted or unsubstituted 5- or 6-membered ring. Preferably $R^5$ represents —$NR^9R^{10}$; the atoms chosen from C, N, O and S necessary to form a substituted, or unsubstituted, 5- or 6-membered ring. Most preferably $R^5$ represents —$NR^9R^{10}$.

$R^6$ represents hydrogen; alkyl, or substituted alkyl, of 1 to 24 carbons. Preferably $R^6$ represents hydrogen; alkyl, or substituted alkyl, of 1 to 5 carbons.

$R^7$ represents hydrogen; alkyl, or substituted alkyl, of 1 to 24 carbons. Preferably $R^7$ represents hydrogen; alkyl, or substituted alkyl, of 1 to 5 carbons.

$R^8$ represents hydrogen; alkyl, or substituted alkyl, of 1 to 24 carbons; aryl, or substituted aryl, of 6 to 24 carbons. Preferably, $R^8$ represents hydrogen; alkyl, or substituted alkyl, of 1 to 24 carbons.

$R^9$ and $R^{10}$ may independently represent hydrogen; alkyl, or substituted alkyl, of 1 to 24 carbons; aryl, or substituted aryl, of 6 to 24 carbons; aralkyl, or substituted aralkyl, of 7 to 25 carbons; the atoms chosen from C, N, O and S necessary to from a substituted, or unsubstituted, 5- or 6-membered ring. $R^9$ and $R^{10}$ may be taken together to represent the atoms chosen from C, N, O and S necessary to form a substituted, or unsubstituted, 5- or 6-membered ring. Preferably $R^9$ and $R^{10}$ independently represent hydrogen; alkyl of 1 to 5 carbons; or $R^9$ and $R^{10}$ are taken together to represent the atoms chosen from C, N, O and S necessary to form a substituted, or unsubstituted, 5- or 6-membered ring.

$R^{11}$ and $R^{12}$ independently represent alkyl, or substituted alkyl, of 1 to 24 carbons; aryl, or substituted aryl, of 6 to 24 carbons.

$R^{13}$ and $R^{14}$ independently represent an alkyl, or substituted alkyl, of 1 to 10 carbons. Preferably, $R^{13}$ and $R^{14}$ independently represent an alkyl, or substituted alkyl, of 2 to 3 carbons.

$R^{15}$ and $R^{16}$ independently represent alkyl, or substituted alkyl, of 1 to 24 carbons.

$R^{17}$ represents a linking group. Preferably $R^{17}$ represents a chemical bond; a linking group comprising C, N, O and S; an alkyl, or substituted alkyl, of 1 to 24 carbons; an aryl, or substituted aryl, of 6 to 24 carbons; or —$N(R^{29})_{3-s}(R^{30})s+$.

$R^{18}$ is an alkyl, or substituted alkyl, of 1 to 24 carbons.

$R^{19}$ is an alkylene, or substituted alkylene, of 1 to 24 carbons.

$R^{20}$, $R^{21}$, $R^{22}$, $R^{23}$, $R^{24}$ and $R^{25}$ independently represent a chemical linkage; an alkyl, or substituted alkyl, of 1 to 10 carbons; an aryl, or substituted aryl, of 6 to 24 carbons; an aralkyl, or substituted aralkyl, of 7–24 carbons; an alkoxy, or substituted alkoxy, of 1 to 10 carbons. Preferably at least one of $R^{20}$, $R^{21}$, $R^{22}$, $R^{23}$, $R^{24}$ and $R^{25}$ independently represents alkyl, or substituted alkyl, of 1 to 5 carbons; aryl, or substituted aryl, of 6 to 12 carbons; or alkoxy, of 1 to 5 carbons.

$R^{26}$, $R^{27}$ and $R^{28}$ independently represent hydrogen; alkyl, or substituted alkyl, of 1 to 5 carbons. Preferably $R^{26}$, $R^{27}$ and $R^{28}$ independently represent hydrogen; alkyl, or substituted alkyl, of 1 to 2 carbons.

$R^{29}$ represents a hydrogen; an alkyl, or substituted alkyl, of 1 to 20 carbons. Preferably, $R^{29}$ represents an alkyl of 1 to 5 carbons.

$R^{30}$ represents an alkylene, or substituted alkylene, of 1 to 20 carbons; arylene, or substituted arylene, of 6 to 24 carbons; aralkylene, or substituted aralkylene, of 6 to 24 carbons. Preferably $R^{30}$ represents an alkylene, or substituted alkylene, of 1 to 5 carbons.

$L^1$ represents methine; substituted methine; or nitrogen.

$L^2$ and $L^3$ independently represent methine; substituted methine; dimethine or substituted dimethine.

$L^4$ represents dimethine or substituted dimethine.

$Z^1$, $Z^2$, $Z^3$, $Z^4$, $Z^5$ and $Z^6$ independently represent the atoms chosen from C, N, O, and S necessary to form a substituted, or unsubstituted, 5- or 6-membered ring. Preferably $Z^1$, $Z^2$, $Z^3$, $Z^4$, $Z^5$ and $Z^6$ independently represent a substituted, or unsubstituted, ketomethylene ring; a substituted, or unsubstituted, pyrazolinone.

l is an integer of 2 to 400,000.

m is an integer of 1 to 40. Preferably m is an integer of 1 to 15.

p is an integer of 0 to 400,000.

n is an integer of at least 2 . Preferably n is an integer of at least 2 to no more than 400,000. More preferably n is an integer of at least 2 and no more than 100. Even more preferably n is an integer of at least 2 to no more than 20. Most preferably n is an integer of at least 2 to no more than 5.

r is an integer of 0 to 5.

w is an integer of 0 to 5.

v is an integer of 0 to 5.

q is an integer of 2 to 4.

s is an integer of 1 to 3.

$X^-$ is a counter ion used to balance the charge of the molecule. Particularly preferred counter ions include, but are not limited to, halide, $ClO_4^-$, $BF_4^-$, $p\text{-}CH_3C_6H_4SO_3^-$.

It would be apparent from the disclosure that L excludes gelatin, hydrophilic colloid, or protein.

The recitation "atoms chosen from C, N, O, and S necessary to from a 5- or 6-membered ring" or the equivalent thereof, refers to substituted or unsubstituted rings. Fused rings may be mentioned as included. Aromatic and aliphatic rings are anticipated as are the rings including but not limited to:

cycloalkyl, particularly cyclopentane and cyclohexane; cycloalkenyl particularly cyclopentene and cyclohexene; indoles; piperidine; piperidyl; piperazinyl; pyrrolidine; pyrrolidinyl; pyrazolidine; pyrimidine; furan; thiophene; oxazine; thiazoline; thiazolidine; thiazole particularly thiazole, 4-methylthiazole, 4-phenylthiazole, 5-methylthiazole, 5-phenylthiazole, 4,5-dimethylthiazole, 4,5-diphenylthiazole, 4-(2-thienyl)-thiazole; benzothiazole particularly benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, 5-hydroxybenzothiazole, 6-hydroxybenzothiazole; naphthothiazole particularly naphtho[1,2]-thiazole, naphtho[2,1]thiazole, 5-methoxynaphtho-[2,1]-thiazole, 5-ethoxynaphtho[2,1]thiazole, 8-methoxynaphtho [1,2]thiazole, 7-methoxynaphtho[1,2]thiazole; thianaphtheno-7',6',4,5-thiazole; oxazole particularly 4-methyloxazole, 5-methyloxazole, 4-phenyloxazole, 4,5-diphenyloxazole, 4-ethyloxazole, 4,5-dimethyloxazole, 5-phenyloxazole; benzoxazole particularly benzoxazole, 5-chlorobenzoxazole, 5-methylbenzoxazole, 5-phenylbenzoxazole, 6-methylbenzoxazole, 5,6-dimethylbenzoxazole, 4,5-dimethylbenzoxazole, 5-methoxybenzoxazole, 5-ethoxybenzoxazole, 5-chlorobenzoxazole, 6-methoxybenzoxazole, 5-hydroxybenzoxazole, 6-hydroxybenzoxazole; naphthoxazole particularly naphtho[1,2]-oxazole, naphtho[2,1]oxazole; thiazoline particularly thiazoline, 4-methylthiazoline; quinoline particularly 2-quinoline, 3-methylquinoline, 5-methylquinoline, 7-methylquinoline, 8-methylquinoline, 6-chloroquinoline, 8-chloroquinoline, 6-methoxyquinoline, 6-ethoxyquinoline, 6-hydroxyquinoline, 8-hydroxyquinoline; quinoline particularly 4-quinoline, 6-methoxyquinoline, 7-methoxyquinoline, 7-methylquinoline, 8-methylquinoline; isoquinoline particularly 1-isoquinoline, 3,4-dihydroisoquinoline, 3-isoquinoline; benzimidazole particularly 1,3-diethylbenzimidazole, 1-ethyl-3-phenylbenzimidazole; 3,3-dialkylindolenine particularly 3,3-dimethylindoline, 3,3,5-trimethylindolenine, 3,3,7-trimethylindolenine; pyridine particularly 2-pyridine, 5-methylpyridine, 4-pyridine; 3,3-dialkylbenz[e]indole particularly 3,3-dimethylbenz[e]indole; tetrazole particularly 1-phenyltetrazole, 1-methyltetrazole; triazine particularly dichlorotriazine; triazole particularly 1-phenyl-triazole, 1-methyltriazole; pyrimidine; thiadiazole particularly 1,3,4-thiadiazole; substituted or unsubstituted pyranose such as D-glucose, D-glucosonic acid or D-galacto-D-mannoglycan; substituted or unsubstituted furanose.

Ketomethylene rings comprise a cyclic hydrocarbon ring with at least one ketone attached thereto. Specifically suitable ketomethylene rings are derived from the following nuclei which may be additionally substituted if so desired: 1,3-indandione, pyrazolone, 2,4,6,-trioxohexahydropyrimidine, 2-thio-4,6,dioxohexahydropyrimidine, 3,5-pyrazolidinedione, 5,7-dioxo-6,7-dihydro-5-thiazolo[3,2-a]pyrimidine, 2-thio-2,4-oxazolidinedione, 5,5-dialkyl-1,3-cylcohexanedione, 2-hydroxy-4H-pyrido[1,2-a]pyrimidin-4-one rhodanine, hydantoin, thiohydantoin, isoxazolone and the like.

The terms "alkyl", "aryl", and "aralkyl" and other groups refer to both unsubstituted and substituted groups unless specified to the contrary. Alkyl can be saturated or unsaturated and unless otherwise specified refers to alkyls of 1 to 24 carbon atoms. Unless otherwise specified the term aryl refers to aryl of 6 to 24 carbons and the term aralkyl refers to aralkyl of 7 to 25 carbons. Preferred substituents include but are not limited to halogen; nitro; carboxyl; hydroxyl; alkoxy; amine; thiol; amide; vinyl; sulfate; cyano and thioether.

The inventive hardeners defined by Compound I are formed by the reaction of carboxylic acid groups with an active imidazolium as postulated in Scheme A. The reaction proceeds very rapidly and can be carried out as a separate process wherein the inventive compound is formed and optionally isolated prior to introduction to the hydrophilic colloid mixture. Alternatively, the carboxylic acid contributor, of Compound II, can be added to a the hydrophilic colloid solution followed by addition of the active imidazolium to form the crosslinker of Compound I in-situ. The term "in-situ" specifically refers to a reaction which occurs within the reaction vessel in the presence of all ingredients from which subsequent reaction is expected. This is distinguished from external reactions wherein the inventive hardener is formed prior to introduction to the hydrophilic colloid.

While not limited to any theory, the reaction of active imidazolium and carboxylic acid is hypothesized to involve a substitution reaction in accordance with the following equation:

Scheme A

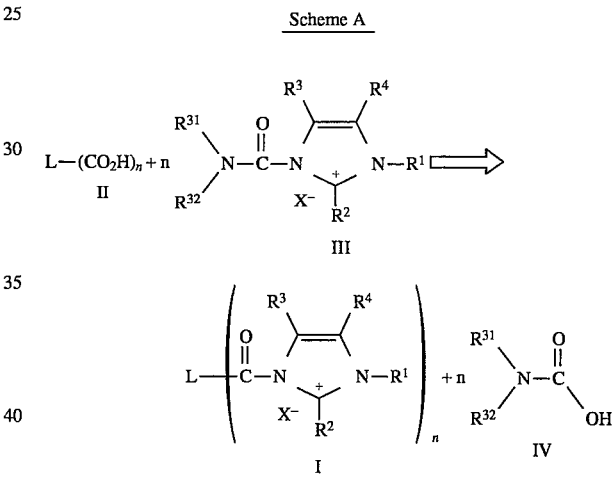

Referring specifically to Compound II of Scheme A, the substituents L and n are as defined above for Compound I. Particularly preferred examples of Compound II include, but are not limited to:

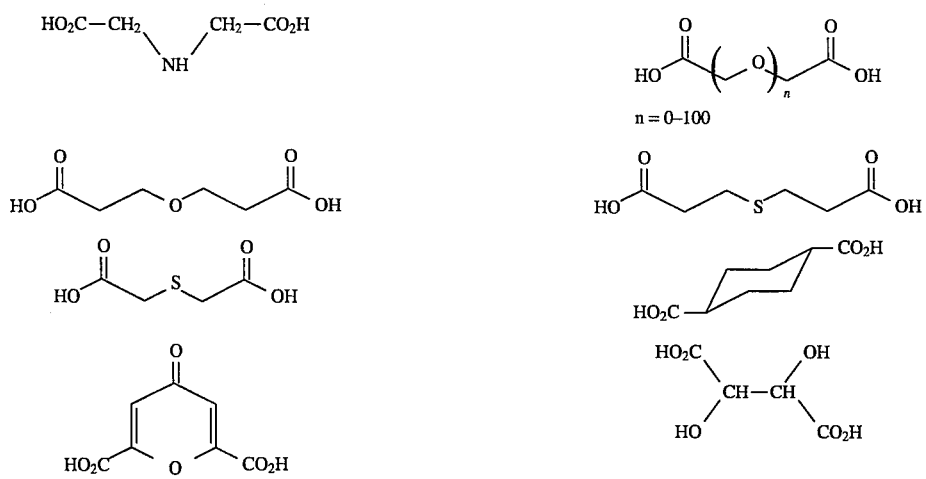

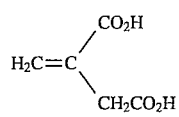
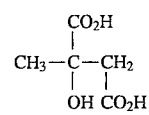
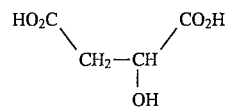
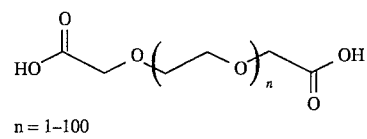
n = 1–100
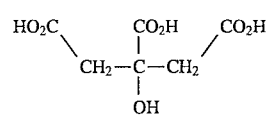
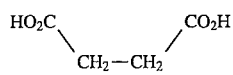
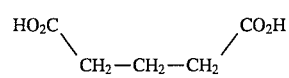
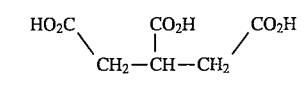
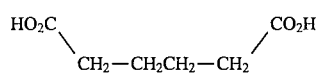
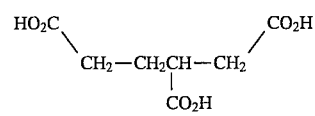
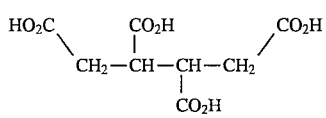
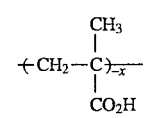
X = 2–400,000
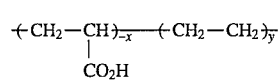
x = 2–400,000
y = 2–400,000
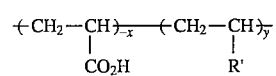
R' = H, —CONH$_2$, —C$_6$H$_5$
x = 2–400,000
y = 0–400,000
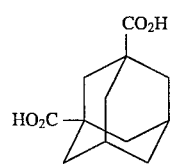
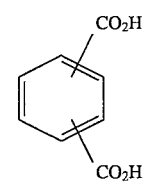
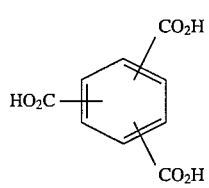
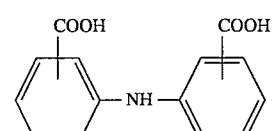
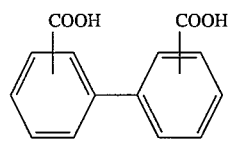
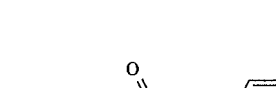
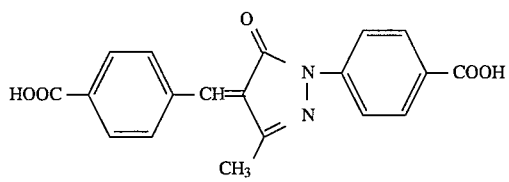
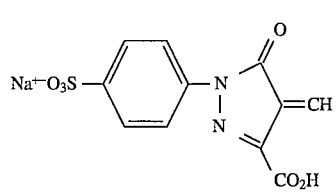
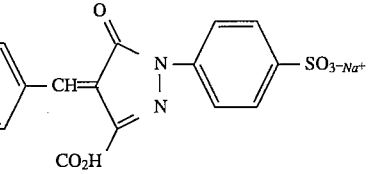

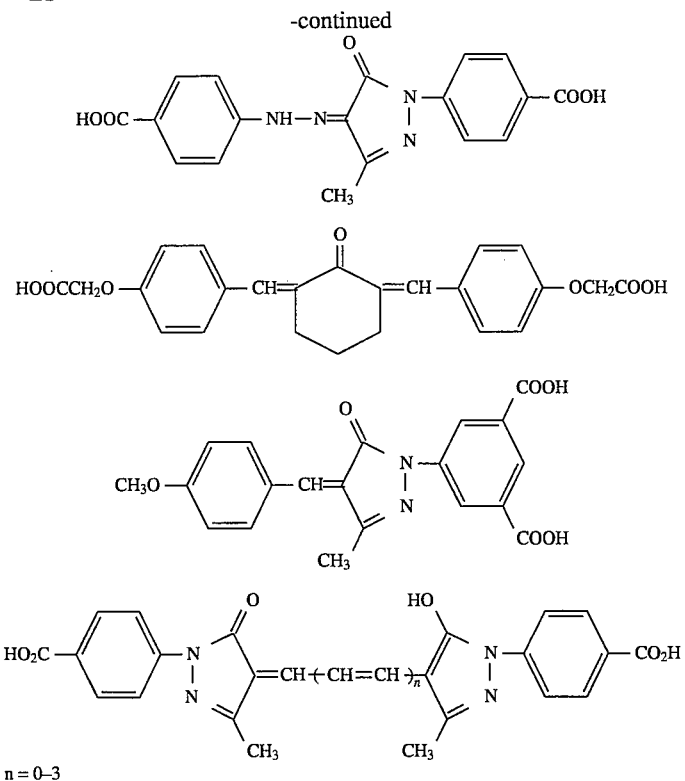

Referring specifically to Compound III of Scheme A. $R^1$, $R^2$, $R^3$, $R^4$ and $X^-$ are defined identically as in Compound I. $R^{31}$ and $R^{32}$ independently represent hydrogen; alkyl, or substituted alkyl, of 1 to 24 carbons; aryl, or substituted aryl, of 6 to 24 carbons; aralkyl, or substituted aralkyl, of 7 to 25 carbons; $R^{31}$ and $R^{32}$ independently may represent, or be taken together to represent, the atoms chosen from C, N, O and S necessary to form a 5- or 6-membered ring.

Particularly preferred examples represented by Compound III include but are not limited to:

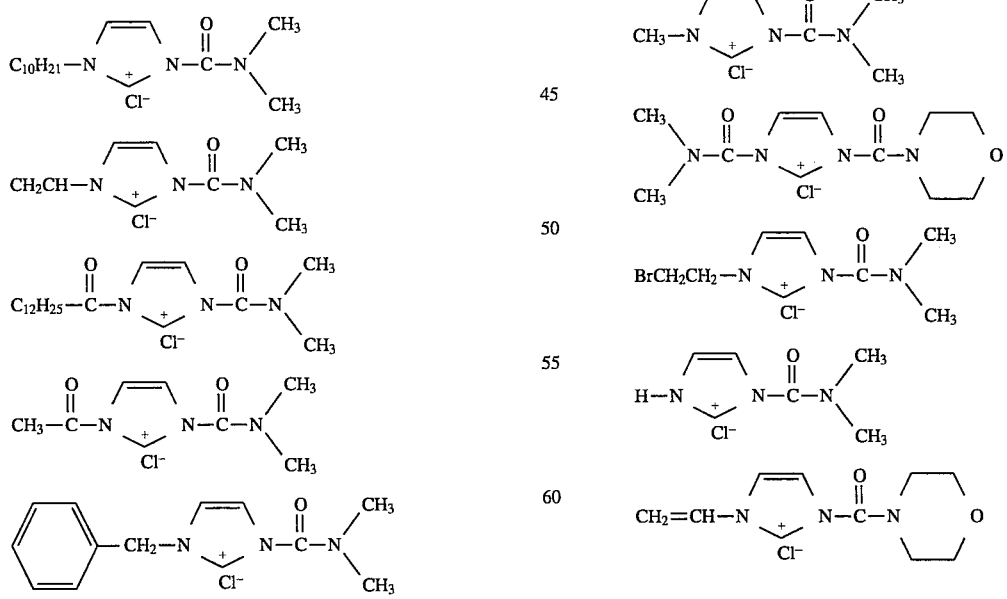

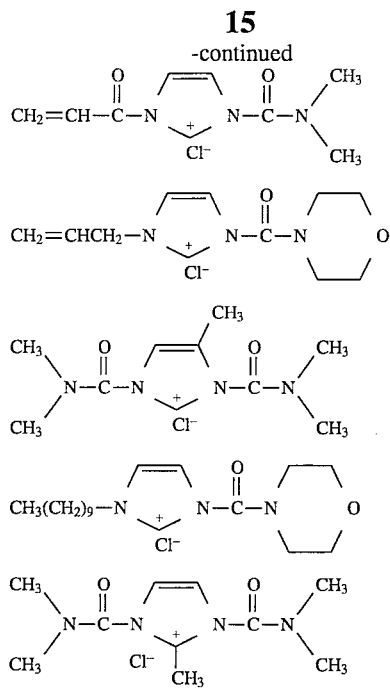
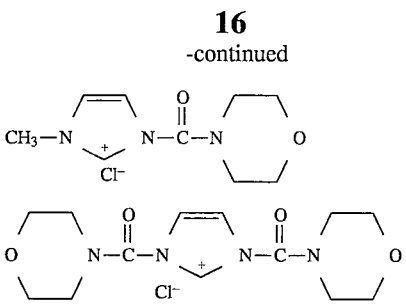
As described herein, compounds chosen from those represented by Compound II in combination with compounds chosen from Compound III will react to form the inventive hardener represented by Compound I in accordance with the previously hypothesized reaction.
Particularly preferred hardeners include but are not limited to:
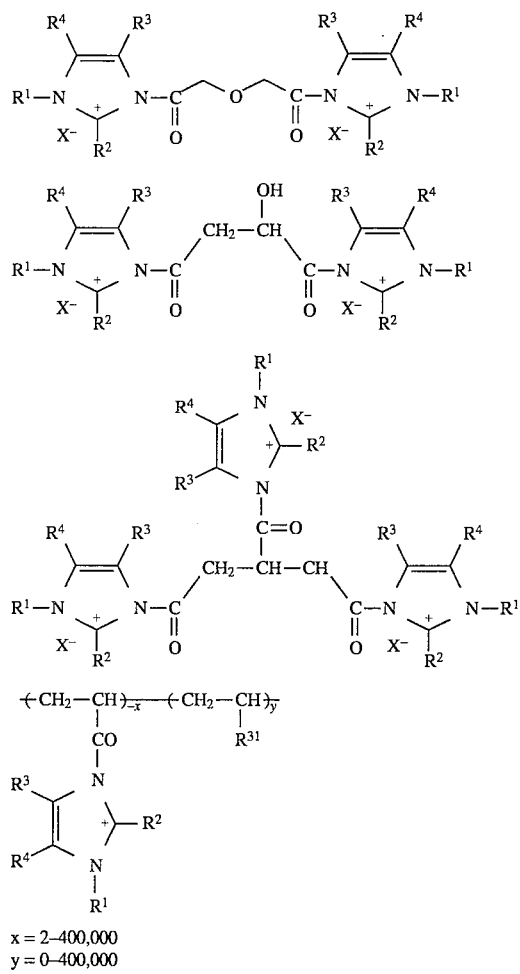
x = 2–400,000
y = 0–400,000

-continued

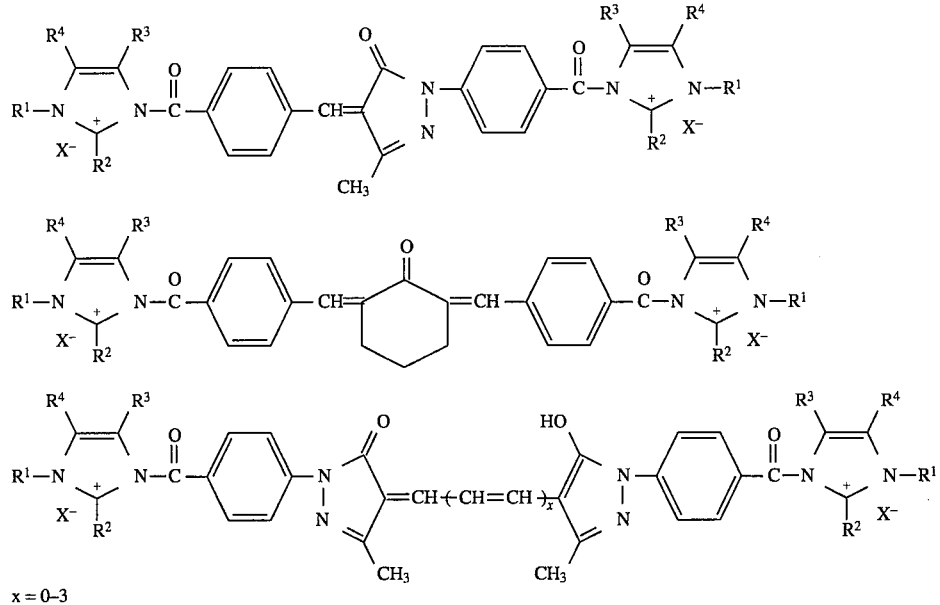

x = 0-3 wherein $R^1$, $R^2$, $R^3$, $R^4$ and X are defined previously and $R^{31}$ represents hydrogen, —$CONH_2$ or —$C_6H_5$.

The structure of the imidazolium ring is known to exist with a delocalized charge. Comparable resonance structures can be drawn including:

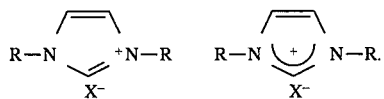

The hardeners of the present invention react rapidly with a hydrophilic colloid and therefore addition of the hardener to a solution containing hydrophilic colloid must be done with care. In a practical sense the addition is typically done just prior to application of the hydrophilic colloid by injection of the hardener into the hydrophilic colloid solution or some similar manner. Preferably, the hardener is dissolved in a suitable solvent such as water, alcohol, dimethylformamide, dimethylsulfoxide and the like. The reaction proceeds at a sufficiently rapid rate that the preferred method of carboxylic acid addition is to coating solution followed by addition of the imidazolium just prior to application of the solution. This is typically referred to as in-line injection since the imidazolium solution is injected into the line carrying the coating solution.

The reaction product IV of Scheme A presumably decomposes yielding a secondary amine and carbon dioxide. The carbon dioxide readily volatilizes.

The amount of hardener solution added depends upon the degree of crosslinking desired. For use in a photographic emulsion the hardener solution is typically added in an amount sufficient to equal 0.01 to 1.0 mmoles of imidazolium per gram of hydrophilic colloid. More preferred is an amount of 0.02 to 0.30 mmoles of imidazolium per gram of hydrophilic colloid. The amount added may be different for different hydrophilic colloids and different applications.

The hardeners of the present invention are most suitable for crosslinking a hydrophilic colloid layer. It is most preferred to use the hardeners of the present invention for a coated layer of hydrophilic colloid. The commercial application includes, but is not limited to, the use of a hardened hydrophilic colloid layer in a photographic element as either a photosensitive layer, an underlayer, an overcoat layer or a dyed layer.

When hardeners of the present invention are used in a hydrophilic colloid solution the pendant amines are hypothesized to nucleophilically attack the carbonyl of the hardener thereby liberating the imidazolium ring and forming an amide bond between the linking group, L, and the hydrophilic colloid postulated for a divalent group in Scheme B. The resulting product is a pair of hydrophilic colloid fractions crosslinked to each other with a bridging group comprising a pair of amide linkages. It would be apparent that a multi-valent linking group (L) could offer additional crosslinking sites. The terms "hardening" and "cross-linking" are used interchangeably in the art to refer to a reaction which couples hydrophilic colloids.

SCHEME B

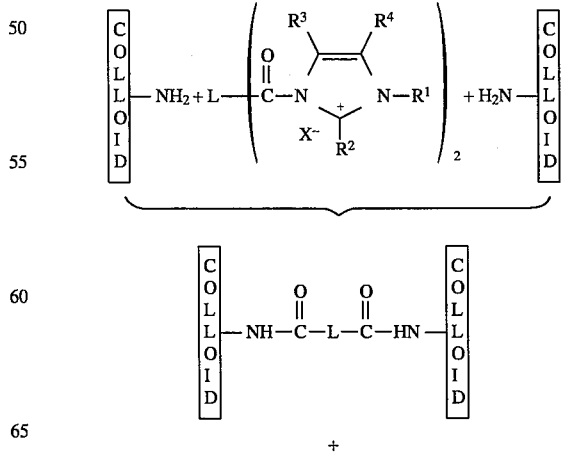

+

-continued
SCHEME B

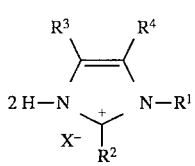

A photosensitive layer typically comprises silver halide dispersed in a hydrophilic colloid binder. The silver halide is optionally chemically and optionally spectrally sensitized as known in the art and the layer may contain other adjuvants such as dyes, stabilizers, development agents, color coupling agents, toners, surfactants, and the like.

An underlayer typically comprises a hydrophilic colloid layer with an optional dye dispersed therein. The overcoat is typically coated supra to the photosensitive layer as protection from abrasion and the like and may comprise dyes, additional surfactants, or other adjuvants as known in the art.

The term "hydrophilic colloid" or its homologues "gelatin" and "protein" are used herein to refer to the protein substances which are derived from collagen. In the context of the present invention "hydrophilic colloid" also refers to substantially equivalent substances such as synthetic analogues of gelatin. Generally gelatin is classified as alkaline gelatin, acidic gelatin or enzymatic gelatin. Alkaline gelatin is obtained from the treatment of collagen with a base such as calcium hydroxide, for example. Acidic gelatin is that which is obtained from the treatment of collagen in acid such as, for example, hydrochloric acid. Enzymatic gelatin is generated with a hydrolase treatment of collagen. The teachings of the present invention are not restricted to gelatin type or the molecular weight of the gelatin.

The film support for the emulsion layers used in the novel process may be any suitable transparent plastic. For example, the cellulosic supports, e.g. cellulose acetate, cellulose triacetate, cellulose mixed esters, etc. may be used. Polymerized vinyl compounds, e.g., copolymerized vinyl acetate and vinyl chloride, polystyrene, and polymerized acrylates may also be mentioned. Preferred films include those formed from the polyesterification product of a dicarboxylic acid and a dihydric alcohol made according to the teachings of Alles, U.S. Pat. No. 2,779,684 and the patents referred to in the specification thereof. Other suitable supports are the polyethylene terephthalate/isophthalates of British Patent 766,290 and Canadian Patent 562,672 and those obtainable by condensing terephthalic acid and dimethyl terephthalate with propylene glycol, diethylene glycol, tetramethylene glycol or cyclohexane 1,4-dimethanol (hexahydro-p-xylene alcohol). The films of Bauer et al., U.S. Pat. No. 3,052,543 may also be used. The above polyester films are particularly suitable because of their dimensional stability.

Meltpoint is measured by observing the melting temperature in 0.1M NaOH for a hardened gelatin coating. Melt time is measured by immersion of the film sample in a 1.5% NaOH solution at 50° C. and drawing the film out of the solution in measured time increments as is standard practice in the art. Water absorption was determined by weighing a dry 10×10 cm film sample, submerging the sample for 30 minutes in an aqueous solution buffered to a pH of approximately 10.0 by a borate buffer, allowing the excess water on the surface to drain off of the film for 1 minute, and weighing the swollen film. Unless otherwise stated Water Absorption (WA) is defined as $$WA\ (\%) = \frac{\text{Wet weight} - \text{Dry weight (mg)}}{\text{Dry Weight}} \times 100$$

In-Situ Preparation of Inventive Hardeners

EXAMPLE 1

A stock solution of 8% Rousselot-LHG gelatin was prepared and split into 100 g aliquots. An 8% solution of hardener (H-1) was added in the amounts shown in Table 1.

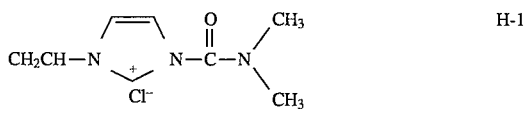

A polymer solution was prepared as a 4% solution of poly(acrylamide) high carboxy modified (MW 200,000) (available as approximately 70% carboxyl from Aldrich Chemical Co., Milwaukee, Wis. cat. no. 19,093-4). The polymer solution was added to the inventive samples in the amounts shown in Table 1. Each sample was brought to a weight of 110 g to insure that dilution differences were eliminated. Where appropriate the solutions were cooled to ambient temperature and held for 24 hrs. The viscosity was measured at 40° C. The inventive samples gelled and a viscosity could not be measured at 40° C. Gelling indicates a high degree of crosslinking in the matrix. The solutions were coated with a #28 Mayer Rod on a subbed polyethylene terephthalate support. Melt times (MT) and water absorption (WA) were recorded and are reported in Table 1.

TABLE 1

| Sample | 4% Polymer Solution (g) | H-1 (g) | cP | MT | WA | |
| --- | --- | --- | --- | --- | --- | --- |
| 1 | — | 0.0 | 10.5 | 3 | 22.6 | Cont. |
| 2 | — | 2.0 | 13.4 | 3 | 17.8 | Cont. |
| 3 | — | 3.0 | 16.6 | 9 | 16.6 | Cont. |
| 4 | — | 7.0 | gel | 18 | 15 | Cont. |
| 5 | 1 | 2.0 | gel | 9 | 16 | Inv. |
| 6 | 2 | 2.0 | * | | | Inv. |

*Analysis could not be accomplished because the material would not melt.
cP is viscosity in centipoise,
MT is melt time in minutes and
WA is percent water absorption.

The data in Table 1 indicates that an increase in hardening is observed with the formation of the inventive hardener. Comparing specifically sample 2 with inventive samples 5 and 6, the same amount of imidazolium was utilized yet the formation of the inventive hardeners increased the viscosity to the point of forming a gel. Sample 5 indicates an increased strength, as defined by the increased melt time, and an decreased water absorption which suggest that the carboxyl groups are reacted.

EXAMPLE 2

A similar experiment to that detailed in Example 1 was done wherein 100 g of an 8% gelatin solution was hardened with 0.5 mmoles of hardeners H-1, H-2 and H-3 per 200 grams of gelatin. A 5% solution of poly(acrylamide) high carboxy modified (MW 200,000) was added to the inventive samples. The results are included in Table 2. Viscosity was measured fresh and after 24 hours.

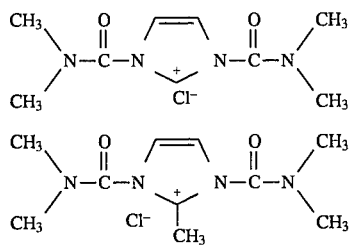

H-2

H-3

TABLE 2

| Sample | 5% Polymer Solution (g) | Hardener | Fresh cP | Aged cP | |
|---|---|---|---|---|---|
| 6 | — | H-1 | 11.9 | 14.7 | Cont. |
| 7 | — | H-2 | 12.0 | 12.6 | Cont. |
| 8 | — | H-3 | 12.0 | 13.8 | Cont. |
| 9 | 1.5 | H-1 | 30.9 | 34.6 | Inv. |
| 10 | 1.5 | H-2 | 30.2 | 34.3 | Inv. |
| 11 | 1.5 | H-3 | 30.1 | 88.5 | Inv. |

The data in Table 2 illustrates the high level of crosslinking available with the inventive hardeners. Comparing, for example, sample 6 with inventive sample 9 an increase in fresh viscosity is observed. This is due, in some part, to the addition of a viscous polymer along with some contribution due to crosslinking. The viscosity after aging indicates the improved crosslinking. The inventive hardeners, formed in-situ, greatly increase the crosslinking.

EXAMPLE 3

An experiment similar to Example 1 was done wherein 100 g of an 8% gelatin solution was hardened with 1 g of a 10% solution of comparative hardener H-4 which acts as an amine-amine cross-linker similar to the inventive hardener.

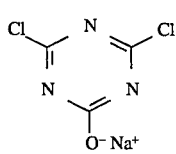

H-4

Hardeners H-1 (1.5 g of 8.2% solution) and H-3 (1.5 g of 10.5% solution) were added both with and without poly(acrylamide) high carboxy modified (PAH) and poly(acrylamide)low carboxy modified (PAL) (MW 200,000 available as approximately 15% carboxy modified from Aldrich Chemical Co., Milwaukee, Wis. Cat. No. 19,092-6). After coating on a subbed polyethylene terephthalate support the melt time (MT) and water absorption (WA) were measured. The results are included in Table 3.

TABLE 3

| Sample | Hardener | Polymer | MT | WA | |
|---|---|---|---|---|---|
| 12 | H-4 | — | 6 | 16.6 | Cont. |
| 13 | H-4 | PAH | 3 | 20.1 | Cont. |
| 14 | H-1 | — | 9 | 17.4 | Cont. |

TABLE 3-continued

| Sample | Hardener | Polymer | MT | WA | |
|---|---|---|---|---|---|
| 15 | H-1 | PAH | 15 | 17.1 | Inv. |
| 16 | H-1 | PAL | 9 | 17.0 | Inv. |
| 17 | H-3 | — | 3 | 18.4 | Cont. |
| 18 | H-3 | PAH | 9 | 18.4 | Inv. |
| 19 | H-3 | PAL | 6 | 20.0 | Inv. |

The hardening observed with hardener H-4 is deleteriously affected by a carboxylic acid compound as indicated by comparing sample 12 with sample 13. The melt time decreases indicating less crosslinking, and the water absorption increases due to the added carboxyl groups. Contrarily, when the appropriate additives are incorporated the inventive hardener is formed. An improved (increased) melt time and/or an improved (decreased) water absorption is observed with the inventive hardener. It would be apparent from the data of Table 3 that a high number of carboxyl groups is better than a low number of carboxyl groups.

EXAMPLE 4

A sensitized silver halide photographic emulsion was coated with a standard anti-abrasion layer on a gelatin-subbed polyester base substrate. The emulsion gelatin was hardened using 10 mmol/200g gelatin of H-4 and 7.5 mmol/100g gelatin of H-3 as injected solutions. In an identical sample diglycolic acid was added to the emulsion solution at 15 mmol/200 g gelatin to give a 1:1 mole ratio between the diacid and the peptide coupler hardener. Inventive hardener IV-1 was formed in-situ. After one month aging the melt time was determined for both samples. The control sample had a melt time of 5 minutes. The sample comprising inventive hardener IV-1 has a melt time of 18 minutes indicating a higher degree of crosslinking with the inventive compound, as determined from melting time.

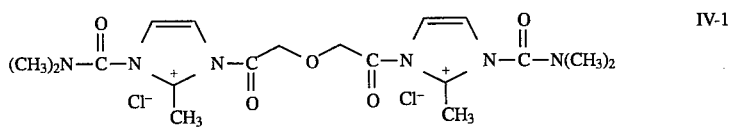

IV-1

EXAMPLE 5

An 8% gelatin solution was prepared with Triton X-100 as a coating aid at pH 5.80. Coatings were prepared on polyester base using a ™26 Mayer rod. Hardener H-2 was added in the amount of 10 mmol/200 g gelatin. For the inventive examples tricarballylic acid (TCA) or malic acid (MA) were added in the amounts indicated in Table 4 prior to hardener addition and coating. The inventive hardener formed was IV-2 and IV-3 when H-2 is combined with TCA and MA respectively. The melt point (MP) and water absorption (WA) are reported in Table 4.

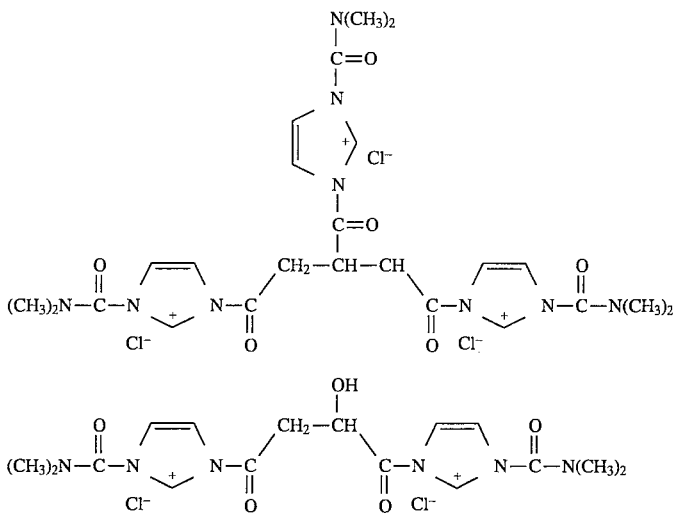

IV-2

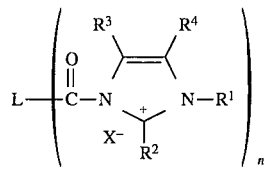

IV-3

TABLE 4

| Acid | Hardener | Amount of Acid mmol/200 g gelatin | MP (°C.) | WA (g/dm²) |
|------|----------|-----------------------------------|----------|------------|
| — | — | — | 77 | 0.46 |
| TCA | IV-2 | 5 | 82 | 0.46 |
| TCA | IV-2 | 10 | 83 | 0.45 |
| Malic | IV-3 | 5 | 84 | 0.35 |
| Malic | IV-3 | 10 | 84 | 0.38 |

Synthesis, Isolation and Utilization Inventive Hardener

EXAMPLE 6

The inventive hardener IV-4 was prepared, analyzed and demonstrated according to the following information.

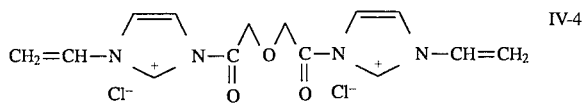

IV-4

1-Vinylimidazole (32 mmol) was added to 50 ml dry THF in a 3-neck round bottom flask and placed under nitrogen atmosphere. Diglycolyl chloride (16 mmol) was dissolved in 15 ml dry THF and placed in an addition funnel under nitrogen atmosphere. The apparatus was placed at 20° C. and the diglycolyl chloride solution was added slowly over 45 minutes. During addition, a thick off-white precipitate formed which was collected by filtration. Upon washing with THF and ether, the product began to oil out, turning light brown. The product was dried in a vacuum dessicator to give a brown-white solid (~86% yield). $^1$H and $^{13}$C NMR data were consistent with the expected product: [$^1$H (D$_2$O ): 8.977(s); 7.806(s); 7.553(s); 5.84(m); 5.44(m); 4.284 (s) $^{13}$C (D$_2$O): 173.89 (carboxyl); 133.77, 128.41, 118.98 (imidazolium); 120.29, 109.71 (vinyl); 67.81 (methylene)] The NMR spectra did not change upon sample preparation in deuterated water suggesting that the product may be air sensitive to give the brown product upon exposure.

This material was screened for hardening ability by coating with an 8% gelatin solution containing only Standapol ES-3 surfactant as coating aid. An amount of the activated diacid material was added in solid form in amounts ranging from 20–60 mmol/200 g gelatin. Hardening activity was observed at the 60 mmol/200 g gelatin level with an observed 3° C. increase in meltpoint versus the control. This example shows that the activated diacid moiety can indeed be synthesized and isolated. In most instances the in-situ preparation is expected to be the method of choice due to the potential for degradation of the inventive hardener upon isolation.

We claim:

1. A hardener for hydrophilic colloid defined by the formula:

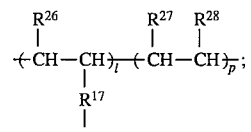

wherein:

L is chosen from a set consisting of alkyl of 1 to 20 carbons with a proviso that L is not —CH$_2$CHOH— or —CH$_2$CHCH$_2$—; phenyl; naphthyl; diphenyl; anthracene; phenanthrene; benzyl; —R$^{11}$—O—R$^{12}$—; —(R$^{13}$O)$_m$R$^{14}$—; —R$^{15}$SR$^{16}$—;

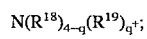

$N(R^{18})_{4-q}(R^{19})_q^+$;

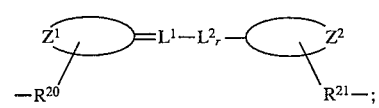

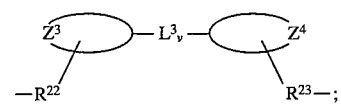

and

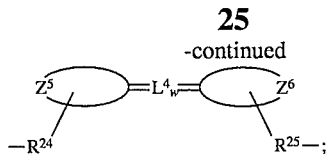

R¹ is an alkyl of 1 to 24 carbons; aryl of 6 to 24 carbons; aralkyl of 7 to 25 carbons; or —C(O)R⁵;

R² is hydrogen; alkyl of 1 to 24 carbons; aryl of 6 to 24 carbons; aralkyl of 7 to 25 carbons; —OR⁶; nitro; carboxyl; mercapto; alkylamino of 1 to 24 carbons; or a halogen;

R³ and R⁴ independently represent hydrogen; alkyl of 1 to 24 carbons; nitro; carboxyl; mercapto; —OR⁷; or R³ and R⁴ taken together represent a 5- or 6-membered ring containing atoms chosen from a set consisting of C, N, O and S;

R⁵ represents an alkyl of 1 to 24 carbons; aryl of 6 to 24 carbons; aralkyl of 7 to 25 carbons; —OR⁸; —CN; —NR⁹R¹⁰; or a 5- or 6-membered ring containing atoms chosen from a set consisting of C, N, O and S;

R⁶ represents hydrogen or alkyl of 1 to 24 carbons;

R⁷ represents hydrogen or alkyl of 1 to 24 carbons;

R⁸ represents hydrogen; alkyl of 1 to 24 carbons or aryl of 6 to 24 carbons;

R⁹ and R¹⁰ independently represent hydrogen; alkyl of 1 to 24 carbons; aryl of 6 to 24 carbons; aralkyl of 7 to 25 carbons; or R⁹ and R¹⁰ taken together represent a 5- or 6-membered ring containing atoms chosen from a set consisting of C, N, O and S;

R¹¹ and R¹² independently represent alkyl of 2 to 24 carbons or aryl of 6 to 24 carbons;

R¹³ and R¹⁴ independently represent alkyl of 1 to 10 carbons;

R¹⁵ and R¹⁶ independently represent alkyl of 1 to 24 carbons;

R¹⁷ represents a chemical bond; an alkyl of 1 to 24 carbons; an aryl of 6 to 24 carbons; or —N(R²⁹)₃₋ₛ(R³⁰)ₛ⁺;

R¹⁸ is an alkyl of 1 to 24 carbons;

R¹⁹ is an alkylene of 1 to 24 carbons;

R²⁰, R²¹, R²², R²³, R²⁴ and R²⁵ independently represent a chemical linkage; an alkyl of 1 to 10 carbons; an aryl of 6 to 24 carbons; an aralkyl of 7–24 carbons; or an alkoxy of 1 to 10 carbons;

R²⁶, R²⁷ and R²⁸ independently represent hydrogen or alkyl of 1 to 5 carbons;

R²⁹ represents hydrogen or an alkyl of 1 to 20 carbons;

R³⁰ represents an alkylene of 1 to 20 carbons; arylene of 6 to 24 carbons; or aralkylene of 6 to 24 carbons;

L¹ represents methine or nitrogen;

L² and L³ independently represent methine or dimethine;

L⁴ represents dimethine;

Z¹, Z², Z³, Z⁴, Z⁵ and Z⁶ independently represent thiazoline; thiazalidine; benzothiazole; benzoxazole; 3-3-dialkylindolenine; 3,3-dialkylbenz[e]indole; 1,3-indandione; pyrazolone; 2,4,6,-trioxohexahydropyrimidine; 2-thio-4,6,dioxohezahydropyrimidine; 3,5-pyrazolidinedione; 5,7-dioxo-6,7-hyhydro-5-thiazolo[3,2-a]pyrimidine,2-thio-2,4oxazolidinedione; 5,5-dialkyl-1, 3-dyclohexanedione; 2-hydroxy-4H-pyrido[1,2-a] pyrimidin-4-one; rhodanine; hydantoin; thiohydantoin; or isoxazolone;

l is an integer of 2 to 400,000;

m is an integer of 1 to 40;

n is an integer of at least 2;

p is an integer of 0 to 400,000;

w is an integer of 0 to 5;

v is an integer of 0 to 5;

q is an integer of 2 to 4;

r is an integer of 0 to 5;

s is an integer of 1 to 3; and

X⁻ is a counter ion to balance charge.

2. The hardener for hydrophilic colloid of claim 1, wherein:

L is chosen from a set consisting of alkyl of 1 to 20 carbons with a proviso that L is not —CH₂CHOH— or —CH₂CHCH₂—; phenyl; naphthyl; diphenyl; anthracene; phenanthrene; benzyl; —R¹¹—O—R¹²—; —(R¹³O)ₘR¹⁴—; —R¹⁵SR¹⁶—;

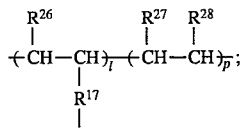

and

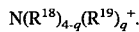

3. The hardener for hydrophilic colloid of claim 2, wherein:

L is chosen from a set consisting of alkyl of 1 to 20 carbons with a proviso that L is not —CH₂CHOH— or —CH₂CHCH₂—; and phenyl.

4. The hardener for hydrophilic colloid of claim 1, wherein:

X⁻ is chosen from a set consisting of a halide, ClO₄⁻, BF₄⁻, and CH₃C₆H₄SO₃⁻.

5. The hardener for hydrophilic colloid of claim 1, wherein:

R⁵ is —NR⁹R¹⁰.

6. The hardener for hydrophilic colloid of claim 5, wherein:

R⁹ and R¹⁰ independently represent alkyl of 1 to 24 carbons; or

R⁹ and R¹⁰ taken together represent morpholine.

7. The hardener for hydrophilic colloid of claim 1, wherein:

R² is hydrogen; alkyl of 1 to 3 carbons; or a halogen.

8. The hardener for hydrophilic colloid of claim 1, wherein:

n is an integer of at least 2 and no more than 400,000.

9. The hardener for hydrophilic colloid of claim 8, wherein:

n is an integer of at least 2 and no more than 20.

10. A hardener for hydrophilic colloid defined by the formula:

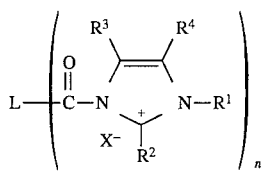

wherein:

L is chosen from a set consisting of alkyl of 1 to 20 carbons with a proviso that L is not —CH$_2$CHOH— or —CH$_2$CHCH$_2$—; phenyl; naphthyl; diphenyl; anthracene; phenanthrene; benzyl; —R$^{11}$—O—R$^{12}$—; —(R$^{13}$O)$_m$R$^{14}$—; —R$^{15}$SR$^{16}$—;

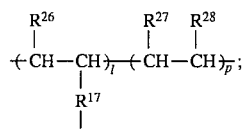

and

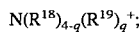

R$^1$ is an alkyl of 1 to 24 carbons; aryl of 6 to 24 carbons; aralkyl of 7 to 25 carbons; or —C(O)R$^5$;

R$^2$ is hydrogen; alkyl 1 to 24 carbons; aryl of 6 to 24 carbons; aralkyl of 7 to 25 carbons; —OR$^6$; nitro; carboxyl; mercapto; alkylamino of 1 to 24 carbons; or a halogen;

R$^3$ and R$^4$ independently represent hydrogen; alkyl of 1 to 24 carbons; nitro; carboxyl; mercapto; —OR$^7$; or R$^3$ and R$^4$ taken together represent a 5- or 6-membered ring containing atoms chosen from a set consisting of C, N, O and S;

R$^5$ represents an alkyl of 1 to 24 carbons; aryl of 6 to 24 carbons, aralkyl of 7 to 25 carbons; —OR$^8$; —CN; —NR$^9$R$^{10}$; or a 5- or 6-membered ring containing atoms chosen from a set consisting of C, N, O and S;

R$^6$ represents hydrogen or alkyl of 1 to 24 carbons;

R$^7$ represents hydrogen or alkyl of 1 to 24 carbons;

R$^8$ represents hydrogen; alkyl of 1 to 24 carbons; or aryl of 6 to 24 carbons;

R$^9$ and R$^{10}$ independently represent hydrogen; alkyl of 1 to 24 carbons; aryl of 6 to 24 carbons; aralkyl of 7 to 25 carbons; or R$^9$ and R$^{10}$ taken together represent a 5- or 6-membered ring containing atoms chosen from a set consisting of C, N and S;

R$^{11}$ and R$^{12}$ independently represent alkyl of 2 to 24 carbons or aryl of 6 to 24 carbons;

R$^{13}$ and R$^{14}$ independently represent alkyl of 1 to 10 carbons;

R$^{15}$ and R$^{16}$ independently represent alkyl 1 to 24 carbons;

R$^{17}$ represents a chemical bond; an alkyl of 1 to 24 carbons; an aryl of 6 to 24 carbons; or —N(R$^{29}$)$_{3-s}$(R$^{30}$)$_s^+$;

R$^{18}$ is an alkyl of 1 to 24 carbons;

R$^{19}$ is an alkylene of 1 to 24 carbons;

R$^{26}$, R$^{27}$ and R$^{28}$ independently represent hydrogen or alkyl of 1 to 5 carbons;

R$^{29}$ represents hydrogen or an alkyl of 1 to 20 carbons;

R$^{30}$ represents an alkylene of 1 to 20 carbons; arylene of 6 to 24 carbons; or aralkylene of 6 to 24 carbons;

l is an integer of 2 to 400,000;

m is an integer of 1 to 40;

n is an integer of at least 2;

p is an integer of 0 to 400,000;

q is an integer of 2 to 4;

s is an integer of 1 to 3; and

X$^-$ is a counter ion to balance charge.

11. The hardener for hydrophilic colloid of claim 10, wherein:

L is chosen from a set consisting of alkyl of 1 to 20 carbons with a proviso that L is not —CH$_2$CHOH— or —CH$_2$CHCH$_2$—; and phenyl.

12. The hardener for hydrophilic colloid of claim 10, wherein:

X$^-$ is chosen from a set consisting of a halide, ClO$_4^-$, BF$_4^-$, and CH$_3$C$_6$H$_4$SO$_3^-$.

13. The hardener for hydrophilic colloid of claim 10, wherein:

R$^5$ is —NR$^9$R$^{10}$.

14. The hardener for hydrophilic colloid of claim 3, wherein:

R$^9$ and R$^{10}$ independently represent alkyl of 1 to 24 carbons; or

R$^9$ and R$^{10}$ taken together represent morpholine.

15. The hardener for hydrophilic colloid of claim 10, wherein:

R$^2$ is hydrogen; alkyl of 1 to 3 carbons; or a halogen.

16. The hardener for hydrophilic colloid of claim 10, wherein:

n is an integer of at least 2 and no more than 400,000.

17. The hardener for hydrophilic colloid of claim 16, wherein:

n is an integer of at least 2 and no more than 20.

* * * * *